US012656326B2

(12) United States Patent
Matsushita et al.

(10) Patent No.: US 12,656,326 B2
(45) Date of Patent: Jun. 16, 2026

(54) CONSTRUCTION METHOD OF ABNORMALITY DIAGNOSIS MODEL, ABNORMALITY DIAGNOSIS METHOD, CONSTRUCTION DEVICE OF ABNORMALITY DIAGNOSIS MODEL, AND ABNORMALITY DIAGNOSIS DEVICE

(71) Applicant: JFE STEEL CORPORATION, Tokyo (JP)

(72) Inventors: Masafumi Matsushita, Tokyo (JP); Takehide Hirata, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 455 days.

(21) Appl. No.: 18/032,239

(22) PCT Filed: Sep. 21, 2021

(86) PCT No.: PCT/JP2021/034601
§ 371 (c)(1),
(2) Date: Apr. 17, 2023

(87) PCT Pub. No.: WO2022/085350
PCT Pub. Date: Apr. 28, 2022

(65) Prior Publication Data
US 2023/0393113 A1     Dec. 7, 2023

(30) Foreign Application Priority Data
Oct. 22, 2020     (JP) .................................. 2020-177364

(51) Int. Cl.
*G01N 33/20*          (2019.01)
(52) U.S. Cl.
CPC .................................. *G01N 33/20* (2013.01)

(58) Field of Classification Search
CPC .......... G01N 33/20; G05B 2219/32356; G05B 2219/33295; G05B 2219/33296;
(Continued)

(56) References Cited

U.S. PATENT DOCUMENTS

2005/0004696 A1*   1/2005   Cribbs ............... G05B 23/0229
                                                          700/148
2010/0095722 A1*   4/2010   Nishiura ................... B21B 1/26
                                                          72/12.2
(Continued)

FOREIGN PATENT DOCUMENTS

CN          107949813 A       4/2018
CN          109996615 A       7/2019
(Continued)

OTHER PUBLICATIONS

Lee et al., "Root Causes Analysis for Beginners," Quality Progress, Jul. 2004, vol. 34, No. 7, pp. 45-53.
(Continued)

*Primary Examiner* — Manuel A Rivera Vargas
(74) *Attorney, Agent, or Firm* — Oliff PLC

(57)                    ABSTRACT

A construction method of an abnormality diagnosis model of a process for sequentially treating a metal material in a plurality of facilities, the construction method includes: creating a first abnormality diagnosis model that learns a relationship between measured values at a same time and an abnormality by using the measured values measured at the same time in a predetermined measurement cycle determined in advance for the plurality of facilities; and creating a second abnormality diagnosis model that learns a relationship between measured values at a same position and an abnormality by using the measured values at the same position of the metal material obtained by compiling the (Continued)

measured values measured in the plurality of facilities for each position of the metal material.

4 Claims, 4 Drawing Sheets

(58) Field of Classification Search
CPC .......... G05B 19/41875; G05B 13/0265; G05B 19/41885; G05B 19/418; B21B 38/00; B21B 37/70; G01M 99/00
See application file for complete search history.

(56) References Cited

U.S. PATENT DOCUMENTS

| | | | | |
|---|---|---|---|---|
| 2010/0219964 A1* | 9/2010 | Hunt | ...................... | G01N 29/46 |
| | | | | 73/579 |
| 2013/0024172 A1* | 1/2013 | Suyama | ............. | G05B 23/0254 |
| | | | | 703/2 |
| 2016/0288038 A1* | 10/2016 | Takaoka | ............. | B01D 46/0095 |
| 2021/0232131 A1 | 7/2021 | Imanari et al. | | |
| 2021/0365018 A1* | 11/2021 | Belouin | ........... | G05B 19/41885 |
| 2022/0187809 A1* | 6/2022 | Hirata | ....................... | G06F 3/14 |
| 2023/0267592 A1* | 8/2023 | Shibasaki | .......... | B23Q 17/0961 |
| | | | | 382/141 |

FOREIGN PATENT DOCUMENTS

| | | | |
|---|---|---|---|
| JP | H01156807 | A | 6/1989 |
| JP | H10-122917 | A | 5/1998 |
| JP | 2011-258113 | A | 12/2011 |
| JP | 4922265 | B2 | 4/2012 |
| JP | 5499900 | B2 | 5/2014 |
| JP | 5651998 | B2 | 1/2015 |
| JP | 2019-074969 | A | 5/2019 |
| TW | 202036016 | A | 10/2020 |
| WO | 2013/011745 | A1 | 1/2013 |
| WO | 2018/096682 | A1 | 5/2018 |
| WO | 2020/049515 | A1 | 3/2020 |

OTHER PUBLICATIONS

Mar. 11, 2024 Extended Search Report issued in European Patent Application No. 21882491.0.
Dec. 7, 2021 International Search Report issued in International Patent Application No. PCT/JP2021/034601.
Jun. 16, 2025 Office Action issued in Chinese Patent Application No. 202180070375.3.
Dec. 4, 2025 Office Action issued in Chinese Patent Application No. 202180070375.3.
Chen et al., Building and Application of Synchronized Data in Tandem Cold Rolling Process, Journal of Northeastern University, vol. 38, No. 2, pp. 239-243, Feb. 15, 2017.
Liu, "Data-Driven Approaches with Mechanistic Analysis for Fault Diagnosis of Cold Rolling Continuous Annealing Processes", Chinese Doctoral Dissertations Full-Text Database—Engineering and Technology, Series I, No. 3, pp. 1-145, Mar. 15, 2017.

* cited by examiner

FIG.3

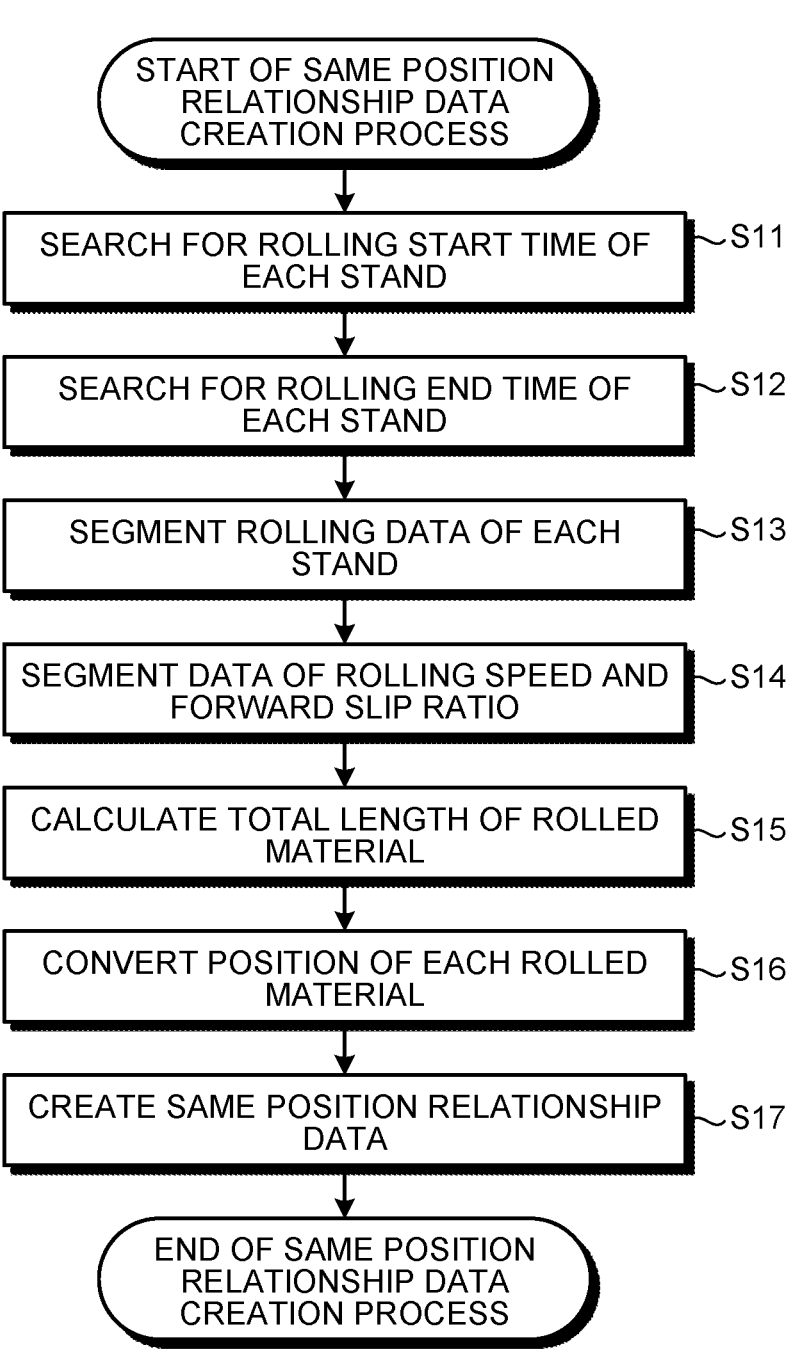

START OF SAME POSITION
RELATIONSHIP DATA
CREATION PROCESS

SEARCH FOR ROLLING START TIME OF
EACH STAND                          ~S11

SEARCH FOR ROLLING END TIME OF
EACH STAND                          ~S12

SEGMENT ROLLING DATA OF EACH
STAND                               ~S13

SEGMENT DATA OF ROLLING SPEED AND
FORWARD SLIP RATIO                  ~S14

CALCULATE TOTAL LENGTH OF ROLLED
MATERIAL                            ~S15

CONVERT POSITION OF EACH ROLLED
MATERIAL                            ~S16

CREATE SAME POSITION RELATIONSHIP
DATA                                ~S17

END OF SAME POSITION
RELATIONSHIP DATA
CREATION PROCESS

FIG.4

CONSTRUCTION METHOD OF ABNORMALITY DIAGNOSIS MODEL, ABNORMALITY DIAGNOSIS METHOD, CONSTRUCTION DEVICE OF ABNORMALITY DIAGNOSIS MODEL, AND ABNORMALITY DIAGNOSIS DEVICE

FIELD

The present invention relates to a construction method of an abnormality diagnosis model, an abnormality diagnosis method, a construction device of the abnormality diagnosis model, and an abnormality diagnosis device.

BACKGROUND

Methods for diagnosing a manufacturing status of a manufacturing process, especially abnormal situations include a model base approach and a data base approach. The model base approach is an approach to construct a model that represents physical or chemical phenomena in a manufacturing process in terms of numerical formula, and diagnose the manufacturing status of the manufacturing process by using the constructed model. Meanwhile, the data base approach is an approach to construct a statistical analytical model from operational data obtained in the manufacturing process and diagnose the manufacturing status of the manufacturing process by using the constructed model.

In the manufacturing process such as a steel process, since many different types and sizes of product are manufactured in one production line, a large number of operation patterns are present. In the manufacturing process such as a blast furnace, since natural materials such as iron ore and coke are used as raw materials, the manufacturing process has a huge variation. Therefore, when diagnosing the manufacturing status of the manufacturing process such as the steel process, there is a limit in the approach based only on the model base approach.

The data base approach includes a diagnosis method for making the operational data when a past abnormality occurred into a database and determining similarity to the current operational data, and a diagnosis method for conversely making the operational data in normal times into a database and determining the difference between the operational data in normal times and the current operational data. However, in the manufacturing process such as the steel process, the number of facilities used for the manufacturing is large, and especially when there are many aging facilities like in Japan, unprecedented troubles often occur. Therefore, there is a limit in the ability of the former diagnosis method based on past trouble cases to predict abnormal situations.

Meanwhile, the latter diagnosis method (diagnosis method using operational data in normal times) includes methods described in Patent Literatures 1 to 4. Specifically, Patent Literatures 1 and 2 describe methods for predicting or detecting abnormal situations in the manufacturing process based on prediction according to a model created using the operational data in normal times. Patent Literatures 3 and 4 describe methods for detecting unusual situations at an early stage by extracting patterns from the operational data in normal times, making the extracted patterns into a library, and determining the difference between the acquired operational data and the library patterns.

CITATION LIST

Patent Literature

Patent Literature 1: WO 2013/011745
Patent Literature 2: Japanese Patent No. 4922265
Patent Literature 3: Japanese Patent No. 5651998
Patent Literature 4: Japanese Patent No. 5499900

SUMMARY

Technical Problem

While the manufacturing process of steel and the like can handle measured values measured by a large number of sensors, many of these measured values are measured for the purpose of operational control and device control. Therefore, as in Patent Literatures 1 to 4, it is not always possible to acquire sufficient measured values that directly indicate the facility status or the cause of abnormality. Even if there is a measured value corresponding one-to-one to such a cause of abnormality, the situation is far from possible to cover all abnormalities only with the measured value.

Meanwhile, recent development in data collection and analysis technology have created an environment for handling a large amount of data referred to as 'big data'. In view of the above-described situation, it can be said that detecting an abnormal situation from the large amount of data in a comprehensive and accurate manner, presenting data related to an abnormality, and leading to prompt maintenance action are necessary for maintaining stable operations. In this case, the large amount of data does not necessarily correspond one-to-one to the cause of abnormality such as in Patent Literatures 1 to 4, and therefore the content of the abnormality to present is not limited to one.

The present invention has been made in view of the above situation, and an object of the present invention is to provide a construction method of an abnormality diagnosis model, an abnormality diagnosis method, an construction device of an abnormality diagnosis model, and an abnormality diagnosis device that can investigate the cause of abnormality at an early stage by detecting abnormal situations from a large amount of measured values acquired in the manufacturing process and classifying and selecting many candidates for the cause of abnormality that does not correspond one-to-one.

Solution to Problem

To solve the problem and achieve the object, a construction method of an abnormality diagnosis model of a process for sequentially treating a metal material in a plurality of facilities, according to the present invention, is the construction method that includes: a first model creation step of creating a first abnormality diagnosis model that learns a relationship between measured values at a same time and an abnormality by using the measured values measured at the same time in a predetermined measurement cycle determined in advance for the plurality of facilities; and a second model creation step of creating a second abnormality diagnosis model that learns a relationship between measured values at a same position and an abnormality by using the measured values at the same position of the metal material obtained by compiling the measured values measured in the plurality of facilities for each position of the metal material.

Moreover, in the construction method of an abnormality diagnosis model according to the present invention, the metal material is a rolled material, and the facilities are rolling mills.

Moreover, in the construction method of an abnormality diagnosis model according to the present invention, the measured values at the same position are calculated based on a ratio of a total length of the rolled material on an exit side of a final rolling mill to a total length of the rolled material on the exit side of a non-final rolling mill by converting the position of the rolled material on the exit side of the non-final rolling mill.

Moreover, in the construction method of an abnormality diagnosis model according to the present invention, the total length of the rolled material on the exit side of the rolling mill is calculated by calculating a strip feeding speed of the rolled material from a roll speed and a forward slip ratio of the rolling mill and integrating the strip feeding speed over time.

Moreover, an abnormality diagnosis method according to the present invention is a method using the abnormality diagnosis model constructed by the construction method of the abnormality diagnosis model according to the present invention. The abnormality diagnosis method includes: a first abnormality diagnosis step of executing abnormality diagnosis by inputting data indicating a relationship between the measured values at the same time into the first abnormality diagnosis model; a second abnormality diagnosis step of executing abnormality diagnosis by inputting data indicating a relationship between the measured values at the same position into the second abnormality diagnosis model; and an abnormality determination step of determining a cause of the abnormality based on a first diagnosis result in the first abnormality diagnosis step and a second diagnosis result in the second abnormality diagnosis step.

Moreover, in the abnormality diagnosis method according to the present invention, the abnormality determination step includes determining the cause of the abnormality based on an abnormality diagnosis table indicating the cause of the abnormality by associating the first diagnosis result with the second diagnosis result.

Moreover, a construction device of an abnormality diagnosis model of a process for sequentially treating a metal material in a plurality of facilities, according to the present invention, is the construction device that includes: a first model creation means for creating a first abnormality diagnosis model that learns a relationship between measured values at a same time and an abnormality by using the measured values measured at the same time in a predetermined measurement cycle determined in advance for the plurality of facilities; and a second model creation means for creating a second abnormality diagnosis model that learns a relationship between measured values at a same position and an abnormality by using the measured values at the same position of the metal material obtained by compiling the measured values measured in the plurality of facilities for each position of the metal material.

Moreover, an abnormality diagnosis device according to the present invention is a device using the abnormality diagnosis model constructed by the construction device of the abnormality diagnosis model according to the present invention. The abnormality diagnosis device includes: a first abnormality diagnosis means for executing abnormality diagnosis by inputting data indicating a relationship between the measured values at the same time into the first abnormality diagnosis model; a second abnormality diagnosis means for executing the abnormality diagnosis by inputting data indicating a relationship between the measured values at the same position into the second abnormality diagnosis model; and an abnormality determination means for determining a cause of the abnormality based on a diagnosis result in the first abnormality diagnosis means and a diagnosis result in the second abnormality diagnosis means.

Advantageous Effects of Invention

The construction method of an abnormality diagnosis model, the abnormality diagnosis method, the construction device of the abnormality diagnosis model, and the abnormality diagnosis device according to the present invention can diagnose an abnormality in machinery and control systems of facilities and an abnormality caused by product quality and shape in distinction by constructing two types of abnormality diagnosis models. Therefore, the cause of abnormality can be investigated at an early stage, the downtime of the facilities can be reduced, and efficient and effective countermeasures against the abnormality can be taken.

BRIEF DESCRIPTION OF DRAWINGS

FIG. 3 is a flow chart illustrating a procedure of a same position relationship data creation process in the abnormality diagnosis device and the model construction device according to the embodiment of the present invention.

FIG. 4 is a flowchart illustrating a procedure of an abnormality diagnosis method executed by the abnormality diagnosis device according to the embodiment of the present invention.

DESCRIPTION OF EMBODIMENTS

A construction method of an abnormality diagnosis model, an abnormality diagnosis method, a construction device of the abnormality diagnosis model, and an abnormality diagnosis device according to an embodiment of the present invention will be described with reference to the drawings.

[Abnormality Diagnosis Device/Model Construction Device]

Figure 1:
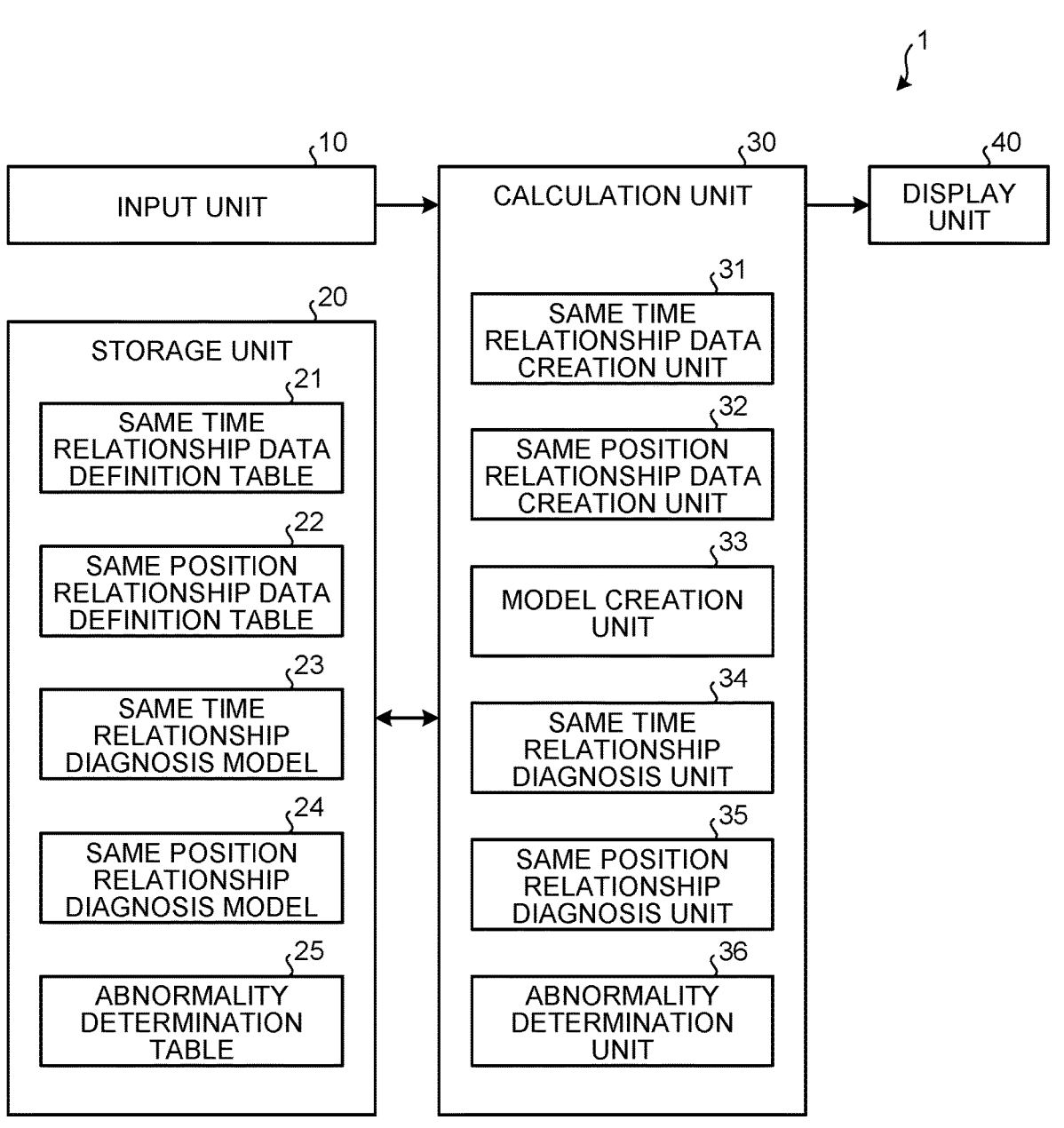
FIG. 1 is a diagram illustrating a schematic configuration of an abnormality diagnosis device and a model construction device according to an embodiment of the present invention.

To begin with, the configuration of the abnormality diagnosis device and the construction device of the abnormality diagnosis model according to the embodiment of the present invention (hereinafter referred to as "model construction device") will be described with reference to FIG. 1. The abnormality diagnosis device and the model construction device are applied to a process of sequentially treating a metal material in a plurality of facilities. The present embodiment describes an example of application to a rolling process for rolling a rolled steel material such as a steel sheet sequentially with a plurality of rolling mills. Note that in the following description, the rolling mill is also referred to as a "stand".

An abnormality diagnosis device 1 includes an input unit 10, a storage unit 20, a calculation unit 30, and a display unit 40. Note that the "model construction device" is implemented by components other than an abnormality determination table 25, a same time relationship diagnosis unit 34, a same position relationship diagnosis unit 35, and an abnormality determination unit 36, out of components of the abnormality diagnosis device 1.

The input unit 10 is an input means for the calculation unit 30, receives actual operational data of a facility to be diagnosed (time-series data) via an information and control system network, and inputs the received operational data into the calculation unit 30 in a predetermined format.

The storage unit 20 includes a recording medium such as an erasable programmable ROM (EPROM), a hard disk drive (HDD), and a removable media. Examples of the removable media include a universal serial bus (USB) memory, and a disk storage medium such as a compact disc (CD), a digital versatile disc (DVD), and a Blu-ray (registered trademark) disc (BD). The storage unit 20 can store an operating system (OS), various programs, various tables, various databases, and the like.

The storage unit 20 stores a same time relationship data definition table 21, a same position relationship data definition table 22, a same time relationship diagnosis model (first abnormality diagnosis model) 23, a same position relationship diagnosis model (second abnormality diagnosis model) 24, and the abnormality determination table 25.

The same time relationship data definition table 21 is a table in which settings necessary for creating same time relationship data by a same time relationship data creation unit 31 are described. The same time relationship data definition table 21 is, for example, the table as illustrated in the following Table 1.

TABLE 1

| Segmentation signal | Signal to indicate start timing of segmentation | Signal to indicate end timing of segmentation |
|---|---|---|
| Signal A(F1) | Final STD load relay signal | Start STD load relay signal |
| Signal B(F2) | Final STD load relay signal | Start STD load relay signal |
| . . . | . . . | . . . |

As illustrated in Table 1, in the same time relationship data definition table 21, signals to indicate start timing and end timing of segmentation are defined for each signal for segmentation of time-series data regarding the actual operation.

The same position relationship data definition table 22 is a table in which settings necessary for creating same position relationship data by a same position relationship data creation unit 32 are described. The same position relationship data definition table 22 is, for example, the table as illustrated in the following Table 2.

TABLE 2

| Segmentation signal | Signal to indicate start and end timing of segmentation | Signal to indicate roll speed of mill to which signal belongs | Signal to indicate forward slip ratio of mill to which signal belongs |
|---|---|---|---|
| Signal A(F1) | F1 load relay signal | F1 strip feeding speed signal | F1 forward slip ratio |
| Signal B(F2) | F2 load relay signal | F2 strip feeding speed signal | F2 forward slip ratio |
| . . . | . . . | . . . | . . . |

As illustrated in Table 2, in the same position relationship data definition table 22, for each signal for segmentation of the time-series data regarding the actual operation, the following signals are defined.

(1) Signal to indicate the start timing and end timing of segmentation (2) Signal to indicate a roll speed of a mill (rolling mill) to which the signal belongs (3) signal to indicate a forward slip ratio of the mill to which the signal belongs The same time relationship diagnosis model 23 is a model that is referred to in the abnormality diagnosis process of the same time relationship data by the same time relationship diagnosis unit 34. The same time relationship diagnosis model 23 is a learned model that has learned the relationship between measured values at the same time and the abnormality, and is created by a model creation unit 33 described later.

The same position relationship diagnosis model 24 is a model that is referred to in the abnormality diagnosis process of the same position relationship data by the same position relationship diagnosis unit 35. The same position relationship diagnosis model 24 is a learned model that has learned the relationship between measured values at the same position and the abnormality, and is created by the model creation unit 33 described later.

The abnormality determination table 25 is a table that is referred to in the abnormality determination process by the abnormality determination unit 36. The abnormality determination table 25 is created based on examples of past operations and the like, and for example, includes a classified table of the cause of abnormality as illustrated in the following Table 3.

The abnormality determination table 25 illustrated in Table 3 has, in order starting from the left column, the following information.

(1) Item observed as an abnormality, cause of abnormality when determined to be abnormal from the same time relationship data (2) Cause of abnormality when determined to be abnormal from the same position relationship data (3) Cause of abnormality when determined to be abnormal from the same time relationship data and the same position relationship data

TABLE 3

| Item observed as abnormality | When determined to be abnormal from same time relationship data | When determined to be abnormal from same position relationship data | When determined to be abnormal from both data |
|---|---|---|---|
| Differential load | Excessive or deficient leveling correction, and so on | Sheet camber, and so on | Pressure gauge failure, and so on |
| Rolling load | Excessive or deficient under pressure compensation control, and so on | Excessive skid mark, and so on | Pressure gauge failure, and so on |
| Tension between stands | Mass flow collapse, and so on | Excessive variation in sheet thickness, and so on | Pressure gauge failure, and so on |
| . . . | . . . | . . . | . . . |

For example, when the results of the abnormality diagnosis process of the same time relationship data by the same time relationship diagnosis unit 34 and the abnormality diagnosis process of the same position relationship data by the same position relationship diagnosis unit 35 are as follows, the abnormality determination unit 36 determines that the causes of abnormality of the differential load, rolling load, and tension between stands are as follows.

Result of the abnormality diagnosis process of the same time relationship data: "differential load: there is an abnormality, rolling load: there is an abnormality, tension between stands: there is no abnormality".

Result of the abnormality diagnosis process of the same position relationship data: "differential load: there is an abnormality, rolling load: there is no abnormality, tension between stands: there is an abnormality".

Cause of abnormality of differential load: "pressure gauge failure".

Cause of abnormality of rolling load: "excessive or deficient under pressure compensation control".

Cause of abnormality of tension between stands: "sheet thickness over-variation".

In each of a case where an abnormality is detected from the same time relationship data, a case where an abnormality is detected from the same position relationship data, and a case where an abnormality is detected from both data, the abnormality diagnosis device 1 according to the embodiment prepares in advance the cause of the abnormality of concern as the abnormality determination table 25. Then, in the abnormality determination process, the cause of abnormality is classified by referring to the abnormality determination table 25.

The calculation unit 30 is implemented, for example, by a processor including a central processing unit (CPU) or the like, a memory (main storage unit) including a random access memory (RAM), a read only memory (ROM), and the like.

The calculation unit 30 implements a function that meets a predetermined purpose by loading a program into a work area of the main storage unit, executing the program, and controlling each component and the like through the execution of the program. The calculation unit functions as the same time relationship data creation unit 31, the same position relationship data creation unit 32, and the model creation unit (first and second model creation means) 33 through the execution of the above-described program. The calculation unit 30 functions as the same time relationship diagnosis unit (first abnormality diagnosis measures) 34, the same position relationship diagnosis unit (second abnormality diagnosis measures) 35, and the abnormality determination unit (abnormality determination measures) 36 through the execution of the above-described program. Note that FIG. 1 illustrates an example in which functions of each unit are implemented, for example, by one computer, but the means for implementing functions of each unit is not particularly limited. For example, a plurality of computers may implement functions of each unit.

Figure 2:
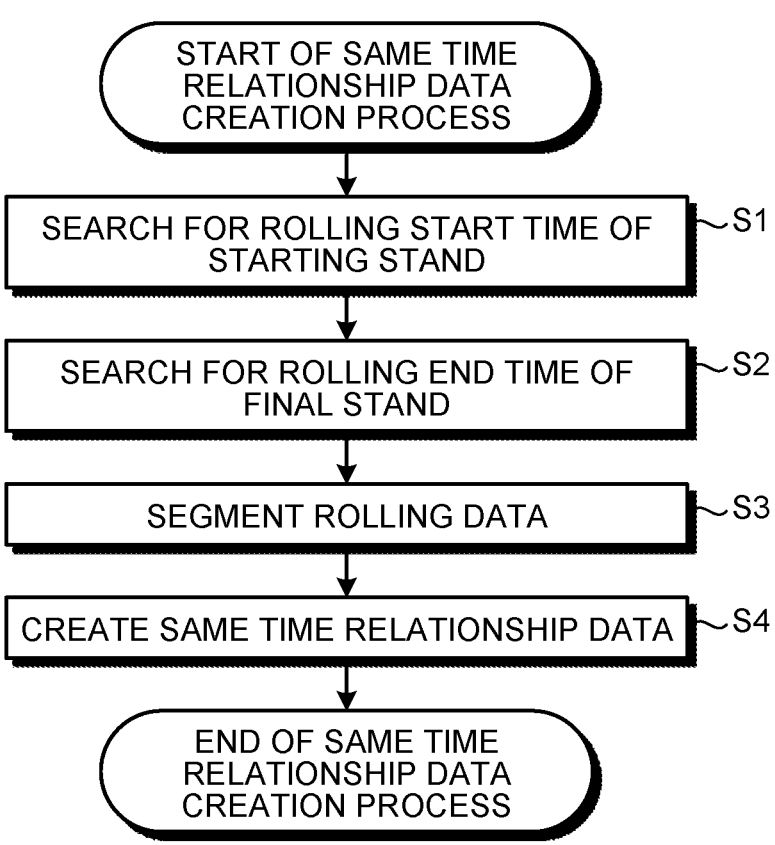
FIG. 2 is a flow chart illustrating a procedure of a same time relationship data creation process in the abnormality diagnosis device and the model construction device according to the embodiment of the present invention.

The same time relationship data creation unit 31 processes the time-series data input from the input unit 10 and creates the same time relationship data indicating the relationship between measured values at the same time. The same time relationship data creation unit 31 specifically refers to the same time relationship data definition table 21 to create the same time relationship data. The same time relationship data creation unit 31 creates the same time relationship data in two situations when creating the same time relationship diagnosis model 23 offline and when executing abnormality diagnosis online (during operation) by the same time relationship diagnosis model 23. One example of the method for creating the same time relationship data will be described below with reference to FIG. 2.

To begin with, the same time relationship data creation unit 31 searches the time-series data about the actual operation for the rolling start time of the starting stand to determine the start of the abnormality diagnosis and the rolling end time of the final stand to determine the end of the abnormality diagnosis (steps S1 and S2). In steps S1 and S2, for example, for a finishing continuous mill including seven stands, by defining the F7 stand as the starting stand and the F1 stand as the final stand, the same time relationship data can be extracted for the stationary part of the rolled material (coil) being rolled in all stands.

Subsequently, between the searched start time and the end time, by segmenting the rolling data (sensor data) of each stand (step S3), the same time relationship data creation unit 31 creates the same time relationship data (step S4).

The same position relationship data creation unit 32 processes the time-series data input from the input unit 10 and creates the same position relationship data indicating the relationship between measured values at the same position. The same position relationship data creation unit 32 specifically refers to the same position relationship data definition table 22 to create the same position relationship data. The same position relationship data creation unit 32 creates the same position relationship data in two situations when creating the same position relationship diagnosis model 24 offline and when executing abnormality diagnosis online (during operation) by the same position relationship diagnosis model 24. One example of the method for creating the same position relationship data will be described below with reference to FIG. 3.

To begin with, the same position relationship data creation unit 32 searches the time-series data about the actual operation for the rolling start time and rolling end time of each stand to be diagnosed (steps S11 and S12). Subsequently, between the searched start time and the end time, the same position relationship data creation unit 32 segments the rolling data (sensor data), and data on the rolling speed (mill speed) and forward slip ratio of the target stand (steps S13 and S14).

Subsequently, the same position relationship data creation unit 32 calculates the total length of the rolled material in each stand (total length of rolled material on the exit side of each rolling mill) from the segmented data (step S15). For example, when the rolling start time of the i-th stand is $t_{i0}$, the forward slip ratio at time t is $f_i(t)$, and the strip feeding speed of the rolled material (hereinafter referred to as "rolling speed") is $v_i(t)$, the position $L_i(t)$ of the data acquired at time t from the tip of the rolled material can be expressed by the following Formula (1). Note that the strip feeding speed of the rolled material can be calculated from the roll speed and the forward slip ratio of the rolling mill.

$$L_i(t) = \int_{t_{i0}}^{t} f_i(t)v_i(t)dt \qquad (1)$$

In the above Formula (1), by setting t as the rolling end time, the total length of the rolled material in the target stand can be calculated. The total length of the final product can be calculated by focusing on the final stand.

Here, when merging data collected in different stands as same position relationship data, the total length of the rolled material in each stand is different. Therefore, the same position relationship data creation unit 32 sets the standard for the length of the rolled material to the length of the final product, that is, the final coil. Then, based on the ratio of the total length of the rolled material on the exit side of the final stand to the total length of the rolled material on the exit side of the target stand (stand other than the final stand), the position of the rolled material on the exit side of the target rolling mill is converted (step S16). With this operation, the same position relationship data is created (step S17).

Note that, for example, when the rolling data is collected by periodic sampling, the obtained data is not evenly spaced when viewed over the total length of the rolled material. Therefore, in this case, it is necessary to obtain evenly spaced same position relationship data by executing an interpolation process. As the interpolation method at that time, for example, linear interpolation can be used when focusing on two adjacent points, and spline interpolation or the like can be used when focusing on three or more points.

In this way, in the process for creating the same position relationship data by the same position relationship data creation unit 32, the total length of the rolled material is calculated by integrating over time the strip feeding speed of the rolled material calculated from the roll speed and the forward slip ratio of the rolling mill. Based on the ratio of the total length of the rolled material similarly calculated from the final stand to the total length of the rolled material in the target stand, data on the position of the target stand in the rolling direction corresponding to the exit side of the final stand is created. This allows the data measured in different stands to be compiled into data about the position in the rolling direction from the tip of the final product.

For the plurality of rolling mills, the model creation unit 33 uses the measured values measured at the same time in a predetermined measurement cycle determined in advance to create the same time relationship diagnosis model 23 that learns the relationship between the measured values at the same time and the abnormality. Note that the above-described "measured values" refer to the same time relationship data created by the same time relationship data creation unit 31.

The model creation unit 33 uses the measured values for the same position of the rolled material with the measured values measured for the plurality of rolling mills compiled for each position of the rolled material to create the same position relationship diagnosis model 24 that has learned the relationship between the measured values at the same position and the abnormality. Note that the above-described "measured values" refer to the same position relationship data created by the same position relationship data creation unit 32.

Note that the method for creating a model by the model creation unit 33 is not particularly limited. As the method for creating a model, a method for detecting an abnormality from the magnitude of discrepancy between the estimated amount derived by the regression model and the actual amount, and a method for detecting an abnormality from a restoration error by a generation model such as an autoencoder can be used. Note that examples of the former method include linear regression, local regression, Lasso regression, Ridge regression, principal component regression, PLS regression, neural network, regression tree, random forest, XG Boost, and the like. The model creation unit 33 stores each of the created same time relationship diagnosis model 23 and the same position relationship diagnosis model 24 in the storage unit 20.

The same time relationship diagnosis unit 34 executes abnormality diagnosis using the same time relationship diagnosis model 23. The same time relationship diagnosis unit 34 executes abnormality diagnosis by inputting the same time relationship data created into the same time relationship data creation unit 31 into the same time relationship diagnosis model 23. The abnormality diagnosis result by the same time relationship diagnosis unit 34 is information obtained by combining items observed as an abnormality (see the left column of Table 3) and whether there is an abnormality in those items, for example, "differential load: there is an abnormality/no abnormality, rolling load: there is an abnormality/no abnormality, and tension between stands: there is an abnormality/no abnormality". The abnormality diagnosis by the same time relationship diagnosis unit 34 can mainly detect an abnormality in the machinery and control system of the facilities.

The same position relationship diagnosis unit 35 executes abnormality diagnosis using the same position relationship diagnosis model 24. The same position relationship diagnosis unit 35 executes abnormality diagnosis by inputting the same position relationship data created by the same position relationship data creation unit 32 into the same position relationship diagnosis model 24. The abnormality diagnosis result by the same position relationship diagnosis unit 35 is information obtained by combining items observed as an abnormality (see Table 3) and whether there is an abnormality in those items, for example, "differential load: there is an abnormality/no abnormality, rolling load: there is an abnormality/no abnormality, and tension between stands: there is an abnormality/no abnormality". The abnormality diagnosis by the same position relationship diagnosis unit 35 can mainly detect an abnormality caused by the product quality and shape.

The abnormality determination unit 36 determines the cause of abnormality based on the diagnosis result by the same time relationship diagnosis unit 34 (first diagnosis result) and the diagnosis result by the same position relationship diagnosis unit 35 (second diagnosis result). The abnormality determination unit 36 determines the cause of abnormality based on the abnormality determination table 25 indicating the cause of abnormality by associating the diagnosis result by the same time relationship diagnosis unit 34 with the diagnosis result by the same position relationship diagnosis unit 35.

The abnormality determination unit 36 specifically determines whether there is an abnormality based on the diagnosis results by the same time relationship diagnosis unit 34 and the same position relationship diagnosis unit 35. Subsequently, the abnormality determination unit 36 classifies the cause of abnormality by comparing the diagnosis results by the same time relationship diagnosis unit 34 and the same position relationship diagnosis unit 35 with the abnormality determination table 25 (see Table 3). Then, the abnormality determination unit 36 outputs these determination results to the display unit 40.

The display unit 40 is implemented, for example, by a display device such as an LCD display or a CRT display. The display unit 40 provides guidance to the operator, for example, by displaying the diagnosis result by the same time relationship diagnosis unit 34, the diagnosis result by the same position relationship diagnosis unit 35, the determination result by the abnormality determination unit 36, and the like based on a display signal input from the calculation unit 30.

[Abnormality Diagnosis Method]

Figure 4:
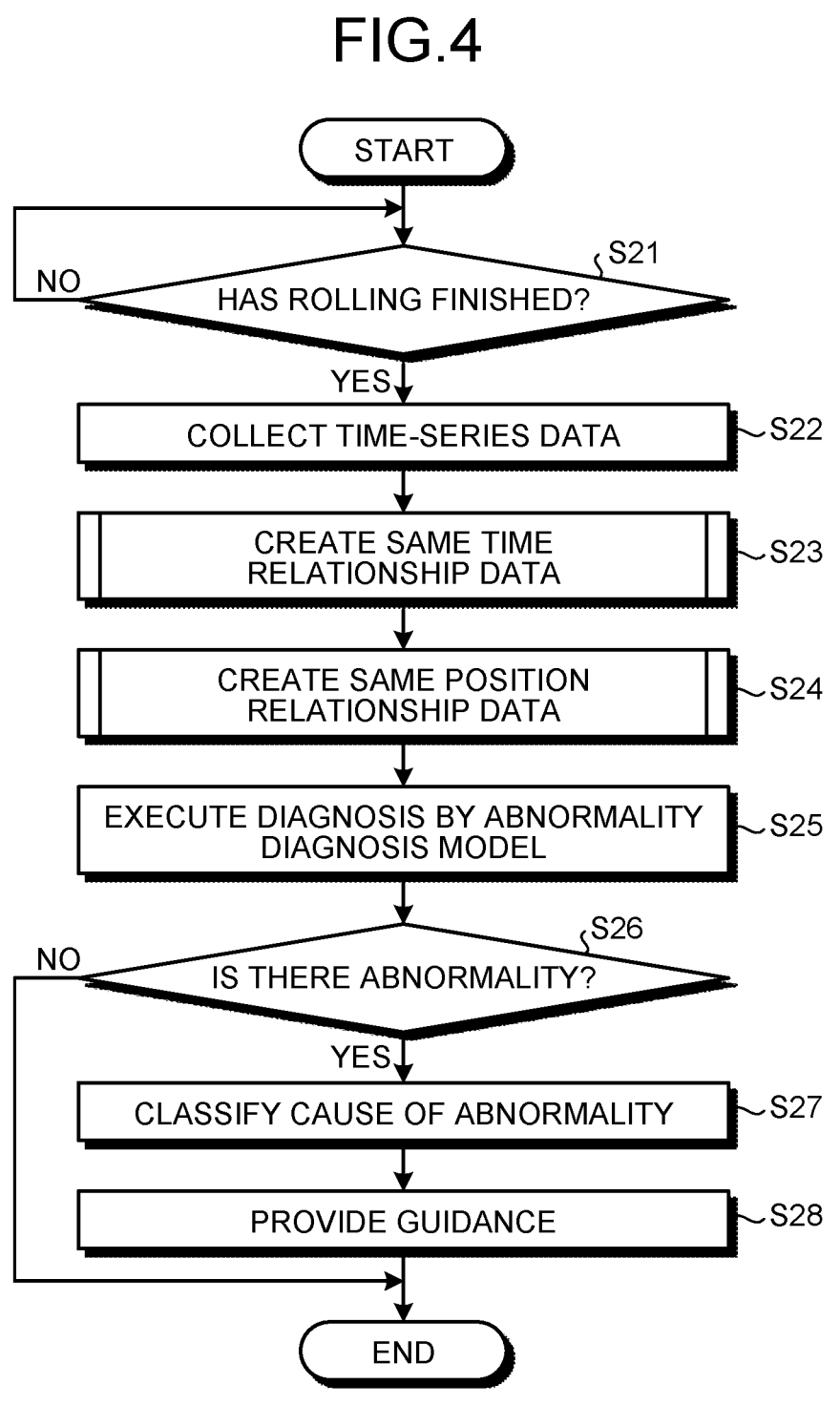

The abnormality diagnosis method by the abnormality diagnosis device 1 according to the embodiment of the present invention will be described with reference to FIG. 4. Note that the abnormality diagnosis method is executed every time rolling of one strip of rolled material finishes in the rolling process.

To begin with, the same time relationship data creation unit 31 and the same position relationship data creation unit 32 determine whether the rolling of the rolled material has finished (step S21). In step S21, it can be determined whether the rolling of the rolled material has finished, for example, based on a winding completion signal of the facility that winds the rolled material, or the like. When it is determined that the rolling of the rolled material has not finished (No in step S21), the same time relationship data creation unit 31 and the same position relationship data creation unit 32 return to step S1. Meanwhile, when it is determined that the rolling of the rolled material has finished (Yes in step S21), the same time relationship data creation unit 31 and the same position relationship data creation unit 32 transition from the state of waiting for events to the diagnosis process and collect the time-series data about the actual operation (step S22).

Subsequently, the same time relationship data creation unit 31 refers to the same time relationship data definition table 21 to create the same time relationship data (step S23). The procedure for creating the same time relationship data in step S23 is the same as in FIG. 2. Subsequently, the same position relationship data creation unit 32 refers to the same position relationship data definition table 22 to create the same position relationship data (step S24). The procedure for creating the same position relationship data in step S24 is the same as in FIG. 3. Note that either of steps S23 and S24 may be executed first, or both may be executed at the same time.

Subsequently, the diagnosis is executed by the abnormality diagnosis model (step S25). In step S25, the abnormality diagnosis process of the same time relationship data by the same time relationship diagnosis unit 34 and the abnormality diagnosis process of the same position relationship data by the same position relationship diagnosis unit 35 are executed.

Subsequently, the abnormality determination unit 36 determines whether there is an abnormality based on the two diagnosis results in step S25 (step S26). In step S26, for example, when either of the two diagnosis results in step S25 includes the item "there is an abnormality", the abnormality determination unit 36 determines that there is an abnormality.

When it is determined that there is an abnormality (Yes in step S26), the abnormality determination unit 36 classifies the cause of abnormality by referring to the abnormality determination table 25 (see Table 3) (step S27). Subsequently, by displaying the abnormality classification result, that is, the candidates for the cause of abnormality on the display unit 40, the abnormality determination unit 36 provides guidance to the operator (step S28). Then, the abnormality determination unit 36 ends this process and transitions to the initial state of waiting for events. Note that when it is determined in step S26 that there is no abnormality (No in step S26), the abnormality determination unit 36 ends this process and transitions to the initial state of waiting for events.

The construction method of an abnormality diagnosis model, the abnormality diagnosis method, the construction device of the abnormality diagnosis model, and the abnormality diagnosis device 1 according to the embodiment executes the following process in the steel rolling process. To begin with, about the time-series data measured with sensors or the like from the rolling mill in operation, information about the position in the rolling direction from the tip of the rolled material is given. Then, two types of data groups are created, data indicating the relationship between measured values at the same position and data indicating the relationship between measured values at the same time, and two types of abnormality diagnosis models are constructed.

In this way, by constructing two types of abnormality diagnosis models, for example, it is possible to distinguish and diagnose an abnormality in the machine and control system of the facility and an abnormality caused by the product quality and shape. Therefore, the cause of abnormality can be investigated at an early stage, the downtime of the facilities can be reduced, and efficient and effective countermeasures against the abnormality can be taken.

The construction method of the abnormality diagnosis model, the abnormality diagnosis method, the construction device of the abnormality diagnosis model, and the abnormality diagnosis device 1 according to the present invention have been specifically described below by means of modes and examples for carrying out the invention. However, the spirit of the present invention is not limited to these descriptions and needs be interpreted broadly based on the claims. It is needless to say that various changes, modifications, and the like based on these descriptions are also included in the spirit of the present invention.

For example, the abnormality diagnosis device 1 according to the embodiment has executed abnormality diagnosis by using two types of abnormality diagnosis models (same time relationship diagnosis model 23, same position relationship diagnosis model 24), but only either one of the abnormality diagnosis models may be used to execute abnormality diagnosis first. Then, abnormality diagnosis by the other abnormality diagnosis model may be executed as necessary.

The abnormality diagnosis device 1 according to the embodiment has described an example of application to the rolling process, but application to, for example, a surface treatment process is possible, besides the rolling process.

REFERENCE SIGNS LIST

1 ABNORMALITY DIAGNOSIS DEVICE
10 INPUT UNIT
20 STORAGE UNIT
21 SAME TIME RELATIONSHIP DATA DEFINITION TABLE
22 SAME POSITION RELATIONSHIP DATA DEFINITION TABLE
23 SAME TIME RELATIONSHIP DIAGNOSIS MODEL
24 SAME POSITION RELATIONSHIP DIAGNOSIS MODEL
30 CALCULATION UNIT
31 SAME TIME RELATIONSHIP DATA CREATION UNIT
32 SAME POSITION RELATIONSHIP DATA CREATION UNIT
33 MODEL CREATION UNIT
34 SAME TIME RELATIONSHIP DIAGNOSIS UNIT
35 SAME POSITION RELATIONSHIP DIAGNOSIS UNIT
36 ABNORMALITY DETERMINATION UNIT
40 DISPLAY UNIT

The invention claimed is:

1. An abnormality diagnosis method comprising:
receiving sensor data from one or more sensors;
constructing an abnormality diagnosis model, of a process for sequentially treating a metal material in a plurality of facilities, by:
creating a first abnormality diagnosis model that learns a relationship between measured values, based on the sensor data, at a same time and an abnormality by using the measured values measured at the same time in a predetermined measurement cycle determined in advance for the plurality of facilities; and creating a second abnormality diagnosis model that learns a relationship between measured values, based on the sensor data, at a same position and an abnormality by using the measured values at the same position of the metal material obtained by compiling the measured values measured in the plurality of facilities for each position of the metal material;

executing a first abnormality diagnosis by inputting data indicating a relationship between the measured values at the same time into the first abnormality diagnosis model;

executing a second abnormality diagnosis by inputting data indicating a relationship between the measured values at the same position into the second abnormality diagnosis model;

determining a cause of the abnormality based on a first diagnosis result in the first abnormality diagnosis and a second diagnosis result in the second abnormality diagnosis; and causing a display to display the cause of the abnormality based on the first diagnosis result and the second diagnosis result, wherein the metal material is a rolled material, the facilities are rolling mills, and the measured values at the same position are calculated based on a ratio of a total length of the rolled material on an exit side of a final rolling mill to a total length of the rolled material on the exit side of a non-final rolling mill by converting the position of the rolled material on the exit side of the non-final rolling mill.

2. The abnormality diagnosis method according to claim 1, wherein the total length of the rolled material on the exit side of the rolling mill is calculated by calculating a strip feeding speed of the rolled material from a roll speed and a forward slip ratio of the rolling mill and integrating the strip feeding speed over time.

3. The abnormality diagnosis method according to claim 1, wherein the determining the cause of the abnormality includes determining the cause of the abnormality based on an abnormality diagnosis table indicating the cause of the abnormality by associating the first diagnosis result with the second diagnosis result.

4. An abnormality diagnosis device comprising:

a construction device of an abnormality diagnosis model of a process for sequentially treating a metal material in a plurality of facilities, the construction device including:

a first model creation means for creating a first abnormality diagnosis model that learns a relationship between measured values, that are based on sensor data from one or more sensors, at a same time and an abnormality by using the measured values measured at the same time in a predetermined measurement cycle determined in advance for the plurality of facilities and a second model creation means for creating a second abnormality diagnosis model that learns a relationship between measured values, based on the sensor data, at a same position and an abnormality by using the measured values at the same position of the metal material obtained by compiling the measured values measured in the plurality of facilities for each position of the metal material;

a first abnormality diagnosis means for executing a first abnormality diagnosis by inputting data indicating a relationship between the measured values at the same time into the first abnormality diagnosis model;

a second abnormality diagnosis means for executing a second abnormality diagnosis by inputting data indicating a relationship between the measured values at the same position into the second abnormality diagnosis model; and an abnormality determination means for determining a cause of the abnormality based on a first diagnosis result in the first abnormality diagnosis means and a second diagnosis result in the second abnormality diagnosis means, wherein the abnormality determination means causes a display to display the cause of the abnormality based on the first diagnosis result and the second diagnosis result, the metal material is a rolled material, the facilities are rolling mills, and the measured values at the same position are calculated based on a ratio of a total length of the rolled material on an exit side of a final rolling mill to a total length of the rolled material on the exit side of a non-final rolling mill by converting the position of the rolled material on the exit side of the non-final rolling mill.

* * * * *